United States Patent [19]
Behan et al.

[11] Patent Number: 5,587,462
[45] Date of Patent: Dec. 24, 1996

[54] BRAIN-DERIVED MEMBRANE-ASSOCIATED CRF BINDING PROTEINS

[75] Inventors: Dominic P. Behan, San Diego; Wylie W. Vale, Jr., La Jolla; Wolfgang H. Fischer, Encinitas, all of Calif.; Philip J. Lowry, Reading, England

[73] Assignee: The Salk Institute For Biological Studies, LaJolla, Calif.

[21] Appl. No.: 149,091

[22] Filed: Nov. 8, 1993

[51] Int. Cl.$^6$ .................. C07K 14/705; C07K 14/695
[52] U.S. Cl. ............................ 530/350; 530/306
[58] Field of Search .................... 530/350, 326, 530/306; 514/13, 2, 12

[56] References Cited

FOREIGN PATENT DOCUMENTS 9213074  8/1992  WIPO .

OTHER PUBLICATIONS

Behan et al., "Isolation of the human plasma corticotrophin-releasing factor-binding protein," *J. Endocrinology* 122(1):23–31 (1989).

Behan et al., "Cloning and structure of the human corticotrophin releasing factor-binding protein gene (CRHBP)," *Genomics* 16:63–68 (1993).

De Souza, et al., "Corticotropin–releasing factor receptors in human pituitary gland: Autoradiographic localization," *Neuroendocrinology* 40:419–422 (1985).

Grigoriadis and De Souza, "The brain corticotropin–releasing factor (CRF) receptor is of lower apparent molecular weight than the CRF receptor in anterior pituitary," *J. Bio. Chem.* 263(22):10927–10931 (1988).

Grigoriadis, et al., "Solubilization of high affinity corticotropin–releasing factor receptors from rat brain: Characterization of an active digitonin–solubilized receptor complex," *Endocrinology* 125(6):3068–3077 (1989).

Potter, et al., "Cloning and characterization of the cDNAs for human and rat corticotropin releasing factor–binding proteins," *Nature* 349:423–426 (1991).

Potter et al., "The central distribution of a corticortropin–releasing factor (CFR)–binding protein predicts multiple sites and modes of interaction with CRF," *P.N.A.S.* 89:4192–4196 (1992).

Suda et al., "Corticotropin–releasing factor–binding protein is a glycoprotein," *Biochem. Biophys. Res. Comm.* 165(2):703–707 (1989).

*Primary Examiner*—Stephen G. Walsh
*Assistant Examiner*—Karen E. Brown
*Attorney, Agent, or Firm*—Fitch, Even, Tabin & Flannery

[57]  ABSTRACT

Isolated, substantially pure mammalian brain-derived membrane-associated CRF-binding proteins and biologically active fragments thereof are provided as well as isolated and purified DNA fragments which encode the CRF binding proteins or biologically active fragments thereof or homologs of other mammalian species. By administering an amount of such CRF binding protein or a fragment thereof effective to modulate receptor activation, it is possible to modulate the action of CRF upon (a) the brain and nervous system, (b) the pituitary particularly for production of ACTH, beta endorphin and cortisol, (c) sites of inflammation, (d) the placenta, (e) the adrenal glands, (f) the gonads or (g) the gastrointestinal tract. Administration of an N-terminal fragment of the protein increases the binding site density for CRF and thus modulates its biological effect in vivo.

11 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 295 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:1:

```
Glu Ala Val Asp His Asp Ser Phe Pro His Leu Ala Gly Gly Ala Ser
  1               5                  10                  15
Pro Lys Arg Glu Leu Glu Gly Glu Pro Leu Tyr Arg Arg Ala Leu Arg
                 20                  25                  30
Cys Val Asp Met Leu Ser Leu Gln Gly Gln Phe Thr Phe Thr Ala Asp
                 35                  40                  45
Arg Arg Gln Leu His Cys Ala Thr Phe Phe Ile Ala Glu Pro Glu Glu
         50                  55                  60
Phe Ile Thr Ile His Tyr Asp Leu Val Ser Ile Asp Cys Leu Arg Gly
 65                  70                  75                  80
Asp Ile Leu Gln Val Phe Asp Gly Trp Ile Leu Lys Gly Glu Lys Phe
                 85                  90                  95
Pro Ser Ser Gln Asp His Pro Leu Pro Thr Thr Glu Arg Tyr Val Asp
                 100                 105                 110
Phe Cys Asp Ser Gly Leu Ser Arg Arg Ser Ile Arg Ser Ser Gln Asn
                 115                 120                 125
Val Ala Met Ile Phe Phe Arg Val His Glu Pro Gly Asn Gly Phe Thr
         130                 135                 140
Ile Thr Val Lys Thr Glu Pro Asn Leu Phe Pro Cys Asn Ile Ile Ser
145                 150                 155                 160
Gln Thr Pro Asn Gly Arg Phe Thr Leu Val Met Pro His Gln His Arg
                 165                 170                 175
Asn Cys Ser Phe Ser Ile Ile Tyr Pro Val Ala Ile Lys Ile Ser Asp
                 180                 185                 190
Leu Thr Leu Gly His Leu Asn Gly Leu Gln Leu Lys Lys Ser Ser Ala
                 195                 200                 205
Gly Cys Gly Gly Ile Gly Asp Phe Val Glu Leu Leu Gly Gly Thr Gly
```

-continued

|  |  | 210 |  |  |  | 215 |  |  |  | 220 |  |  |  |
|---|---|---|---|---|---|---|---|---|---|---|---|---|---|
| Leu 225 | Asp | Pro | Ser | Lys | Met 230 | Leu | Leu | Leu | Ala | Asp 235 | Leu | Cys | Tyr | Pro | Leu 240 |
| Arg | Gly | Pro | Ala | Gln 245 | Met | Lys | Val | Gly | Cys 250 | Asp | His | Thr | Val | Leu 255 | Arg |
| Met | Val | Ser | Ser 260 | Gly | Lys | Leu | Leu | Asn 265 | Arg | Val | Thr | Phe 270 | Glu | Tyr | Arg |
| Lys | Leu | Glu 275 | Pro | Tyr | Glu | Leu | Glu 280 | Asn | Pro | Asn | Gly | Asn 285 | Ser | Ile | Gln |
| Glu | Phe 290 | Cys | Leu | Ser | Thr | Leu 295 |

( 2 ) INFORMATION FOR SEQ ID NO:2:

( i ) SEQUENCE CHARACTERISTICS:
      ( A ) LENGTH: 258 amino acids
      ( B ) TYPE: amino acid
      ( C ) STRANDEDNESS: single
      ( D ) TOPOLOGY: unknown ( i i ) MOLECULE TYPE: protein ( x i ) SEQUENCE DESCRIPTION: SEQ ID NO:2:

| Glu 1 | Ala | Val | Asp | His 5 | Asp | Ser | Phe | Pro | Leu 10 | Ala | Gly | Gly | Ala | Ser 15 |
|---|---|---|---|---|---|---|---|---|---|---|---|---|---|---|
| Pro | Lys | Arg | Glu 20 | Leu | Glu | Gly | Glu | Pro 25 | Glu | Glu | Phe | Ile | Thr 30 | Ile | His |
| Tyr | Asp | Leu 35 | Val | Ser | Ile | Asp | Cys 40 | Leu | Arg | Gly | Asp | Ile 45 | Leu | Gln | Val |
| Phe | Asp 50 | Gly | Trp | Ile | Leu | Lys 55 | Gly | Glu | Lys | Phe | Pro 60 | Ser | Ser | Gln | Asp |
| His 65 | Pro | Leu | Pro | Thr | Thr 70 | Glu | Arg | Tyr | Val | Asp 75 | Phe | Cys | Asp | Ser | Gly 80 |
| Leu | Ser | Arg | Arg | Ser 85 | Ile | Arg | Ser | Ser | Gln 90 | Asn | Val | Ala | Met | Ile 95 | Phe |
| Phe | Arg | Val | His 100 | Glu | Pro | Gly | Asn | Gly 105 | Phe | Thr | Ile | Thr | Val 110 | Lys | Thr |
| Glu | Pro | Asn 115 | Leu | Phe | Pro | Cys | Asn 120 | Ile | Ile | Ser | Gln | Thr 125 | Pro | Asn | Gly |
| Arg | Phe 130 | Thr | Leu | Val | Met | Pro 135 | His | Gln | His | Arg | Asn 140 | Cys | Ser | Phe | Ser |
| Ile 145 | Ile | Tyr | Pro | Val | Ala 150 | Ile | Lys | Ile | Ser | Asp 155 | Leu | Thr | Leu | Gly | His 160 |
| Leu | Asn | Gly | Leu | Gln 165 | Leu | Lys | Lys | Ser | Ser 170 | Ala | Gly | Cys | Gly | Gly 175 | Ile |
| Gly | Asp | Phe | Val 180 | Glu | Leu | Leu | Gly | Gly 185 | Thr | Gly | Leu | Asp | Pro 190 | Ser | Lys |
| Met | Leu | Leu 195 | Leu | Ala | Asp | Leu | Cys 200 | Tyr | Pro | Leu | Arg | Gly 205 | Pro | Ala | Gln |
| Met | Lys 210 | Val | Gly | Cys | Asp | His 215 | Thr | Val | Leu | Arg | Met 220 | Val | Ser | Ser | Gly |
| Lys 225 | Leu | Leu | Asn | Arg | Val 230 | Thr | Phe | Glu | Tyr | Arg 235 | Lys | Leu | Glu | Pro | Tyr 240 |
| Glu | Leu | Glu | Asn | Pro 245 | Asn | Gly | Asn | Ser | Ile 250 | Gln | Glu | Phe | Cys | Leu 255 | Ser |
| Thr | Leu |

( 2 ) INFORMATION FOR SEQ ID NO:3:

( i ) SEQUENCE CHARACTERISTICS:
        ( A ) LENGTH: 552 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..552

( x i ) SEQUENCE DESCRIPTION: SEQ ID NO:3:

```
TTT  CCA  CAC  CTC  GCC  GGT  GGC  GCC  AGT  CCG  AAG  CGG  GAG  CTG  GAG  GGG      48
Phe  Pro  His  Leu  Ala  Gly  Gly  Ala  Ser  Pro  Lys  Arg  Glu  Leu  Glu  Gly
 1                   5                        10                       15

GAG  CCG  CTG  TAC  CGC  CGC  GCT  CTG  CGG  TGC  GTG  GAC  ATG  CTG  AGC  CTC      96
Glu  Pro  Leu  Tyr  Arg  Arg  Ala  Leu  Arg  Cys  Val  Asp  Met  Leu  Ser  Leu
           20                        25                       30

CAG  GGC  CAG  TTC  ACC  TTC  ACC  GCC  GAC  CGG  CGC  CAG  CTA  CAC  TGC  GCC     144
Gln  Gly  Gln  Phe  Thr  Phe  Thr  Ala  Asp  Arg  Arg  Gln  Leu  His  Cys  Ala
      35                        40                       45

ACA  TTC  TTC  ATC  GCA  GAG  CCG  GAG  GAG  TTC  ATC  ACC  ATC  CAC  TAC  GAT     192
Thr  Phe  Phe  Ile  Ala  Glu  Pro  Glu  Glu  Phe  Ile  Thr  Ile  His  Tyr  Asp
      50                        55                       60

CTG  GTC  TCC  ATC  GAC  TGT  CTG  AGG  GGC  GAC  ATC  CTG  CAG  GTA  TTT  GAT     240
Leu  Val  Ser  Ile  Asp  Cys  Leu  Arg  Gly  Asp  Ile  Leu  Gln  Val  Phe  Asp
 65                       70                       75                       80

GGT  TGG  ATT  CTC  AAG  GGG  GAG  AAA  TTC  CCC  AGT  TCC  CAG  GAT  CAC  CCT     288
Gly  Trp  Ile  Leu  Lys  Gly  Glu  Lys  Phe  Pro  Ser  Ser  Gln  Asp  His  Pro
                     85                        90                       95

CTC  CCC  ACC  ACT  GAG  AGG  TAC  GTA  GAT  TTC  TGT  GAC  AGT  GGT  CTG  AGC     336
Leu  Pro  Thr  Thr  Glu  Arg  Tyr  Val  Asp  Phe  Cys  Asp  Ser  Gly  Leu  Ser
                100                      105                      110

AGA  AGG  AGC  ATC  AGA  TCC  TCC  CAG  AAC  GTG  GCC  ATG  ATC  TTC  TTC  CGG     384
Arg  Arg  Ser  Ile  Arg  Ser  Ser  Gln  Asn  Val  Ala  Met  Ile  Phe  Phe  Arg
           115                      120                      125

GTC  CAT  GAG  CCA  GGA  AAT  GGA  TTC  ACA  ATA  ACC  GTG  AAG  ACA  GAG  CCT     432
Val  His  Glu  Pro  Gly  Asn  Gly  Phe  Thr  Ile  Thr  Val  Lys  Thr  Glu  Pro
      130                      135                      140

AAC  CTC  TTC  CCC  TGC  AAT  ATC  ATC  TCC  CAG  ACC  CCC  AAT  GGA  AGG  TTT     480
Asn  Leu  Phe  Pro  Cys  Asn  Ile  Ile  Ser  Gln  Thr  Pro  Asn  Gly  Arg  Phe
145                      150                      155                      160

ACT  CTG  GTC  ATG  CCG  CAT  CAG  CAT  CGA  AAC  TGC  AGC  TTC  TCC  ATC  ATT     528
Thr  Leu  Val  Met  Pro  His  Gln  His  Arg  Asn  Cys  Ser  Phe  Ser  Ile  Ile
                165                      170                      175

TAT  CCT  GTA  GCG  ATC  AAA  ATA  TCC                                              552
Tyr  Pro  Val  Ala  Ile  Lys  Ile  Ser
                180
```

( 2 ) INFORMATION FOR SEQ ID NO:4:

( i ) SEQUENCE CHARACTERISTICS:
        ( A ) LENGTH: 441 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..441

5,587,462

-continued ( x i ) SEQUENCE DESCRIPTION: SEQ ID NO:4:

| TTT | CCA | CAC | CTC | GCC | GGT | GGC | GCC | AGT | CCG | AAG | CGG | GAG | CTG | GAG | GGG | 48 |
| Phe | Pro | His | Leu | Ala | Gly | Gly | Ala | Ser | Pro | Lys | Arg | Glu | Leu | Glu | Gly | |
| 1 | | | | 5 | | | | | 10 | | | | | 15 | | |

| GAG | CCG | GAG | GAG | TTC | ATC | ACC | ATC | CAC | TAC | GAT | CTG | GTC | TCC | ATC | GAC | 96 |
| Glu | Pro | Glu | Glu | Phe | Ile | Thr | Ile | His | Tyr | Asp | Leu | Val | Ser | Ile | Asp | |
| | | | 20 | | | | | 25 | | | | | 30 | | | |

| TGT | CTG | AGG | GGC | GAC | ATC | CTG | CAG | GTC | TTT | GAT | GGT | TGG | ATT | CTC | AAG | 144 |
| Cys | Leu | Arg | Gly | Asp | Ile | Leu | Gln | Val | Phe | Asp | Gly | Trp | Ile | Leu | Lys | |
| | | 35 | | | | | 40 | | | | | 45 | | | | |

| GGG | GAG | AAA | TTC | CCC | AGT | TCC | CAG | GAT | CAC | CCT | CTC | CCC | ACC | ACT | GAG | 192 |
| Gly | Glu | Lys | Phe | Pro | Ser | Ser | Gln | Asp | His | Pro | Leu | Pro | Thr | Thr | Glu | |
| | 50 | | | | | 55 | | | | | 60 | | | | | |

| AGG | TAC | GTA | GAT | TTC | TGT | GAC | AGT | GGT | CTG | AGC | AGA | AGG | AGC | ATC | AGA | 240 |
| Arg | Tyr | Val | Asp | Phe | Cys | Asp | Ser | Gly | Leu | Ser | Arg | Arg | Ser | Ile | Arg | |
| 65 | | | | | 70 | | | | | 75 | | | | | 80 | |

| TCC | TCC | CAG | AAC | GTG | GCC | ATG | ATC | TTC | TTC | CGG | GTC | CAT | GAG | CCA | GGA | 288 |
| Ser | Ser | Gln | Asn | Val | Ala | Met | Ile | Phe | Phe | Arg | Val | His | Glu | Pro | Gly | |
| | | | | 85 | | | | | 90 | | | | | 95 | | |

| AAT | GGA | TTC | ACA | ATA | ACC | GTG | AAG | ACA | GAG | CCT | AAC | CTC | TTC | CCC | TGC | 336 |
| Asn | Gly | Phe | Thr | Ile | Thr | Val | Lys | Thr | Glu | Pro | Asn | Leu | Phe | Pro | Cys | |
| | | | 100 | | | | | 105 | | | | | 110 | | | |

| AAT | AGC | ATC | TCC | CAG | ACC | CCG | AAT | GGA | AGG | TTT | ACT | CTG | GTC | ATG | CCG | 384 |
| Asn | Ser | Ile | Ser | Gln | Thr | Pro | Asn | Gly | Arg | Phe | Thr | Leu | Val | Met | Pro | |
| | | 115 | | | | | 120 | | | | | 125 | | | | |

| CAT | CAG | CAT | CGC | AAC | TGC | AGC | TTC | TCC | ATC | ATT | TAT | CCT | GTA | GCG | ATC | 432 |
| His | Gln | His | Arg | Asn | Cys | Ser | Phe | Ser | Ile | Ile | Tyr | Pro | Val | Ala | Ile | |
| | 130 | | | | | 135 | | | | | 140 | | | | | |

| AAA | ATA | TCC | | | | | | | | | | | | | | 441 |
| Lys | Ile | Ser | | | | | | | | | | | | | | |
| 145 | | | | | | | | | | | | | | | | |

( 2 ) INFORMATION FOR SEQ ID NO:5:

( i ) SEQUENCE CHARACTERISTICS:
      ( A ) LENGTH: 678 base pairs
      ( B ) TYPE: nucleic acid
      ( C ) STRANDEDNESS: unknown
      ( D ) TOPOLOGY: unknown ( i i ) MOLECULE TYPE: DNA (genomic)

( i x ) FEATURE:
      ( A ) NAME/KEY: CDS
      ( B ) LOCATION: 1..678

( x i ) SEQUENCE DESCRIPTION: SEQ ID NO:5:

| GAT | CTG | GTC | TCC | ATC | GAC | TGT | CTG | AGG | GGC | GAC | ATC | CTG | CAG | GTA | TTT | 48 |
| Asp | Leu | Val | Ser | Ile | Asp | Cys | Leu | Arg | Gly | Asp | Ile | Leu | Gln | Val | Phe | |
| 1 | | | | 5 | | | | | 10 | | | | | 15 | | |

| GAT | GGT | TGG | ATT | CTC | AAG | GGG | GAG | AAA | TTC | CCC | AGT | TCC | CAG | GAT | CAC | 96 |
| Asp | Gly | Trp | Ile | Leu | Lys | Gly | Glu | Lys | Phe | Pro | Ser | Ser | Gln | Asp | His | |
| | | | 20 | | | | | 25 | | | | | 30 | | | |

| CCT | CTC | CCC | ACC | ACT | GAG | AGG | TAC | GTA | GAT | TTC | TGT | GAC | AGT | GGT | CTG | 144 |
| Pro | Leu | Pro | Thr | Thr | Glu | Arg | Tyr | Val | Asp | Phe | Cys | Asp | Ser | Gly | Leu | |
| | | 35 | | | | | 40 | | | | | 45 | | | | |

| AGC | AGA | AGG | AGC | ATC | AGA | TCC | TCC | CAG | AAC | GTG | GCC | ATG | ATC | TTC | TTC | 192 |
| Ser | Arg | Arg | Ser | Ile | Arg | Ser | Ser | Gln | Asn | Val | Ala | Met | Ile | Phe | Phe | |
| | 50 | | | | | 55 | | | | | 60 | | | | | |

| CGG | GTC | CAT | GAG | CCA | GGA | AAT | GGA | TTC | ACA | ATA | ACC | GTG | AAG | ACA | GAG | 240 |
| Arg | Val | His | Glu | Pro | Gly | Asn | Gly | Phe | Thr | Ile | Thr | Val | Lys | Thr | Glu | |
| 65 | | | | | 70 | | | | | 75 | | | | | 80 | |

| CCT | AAC | CTC | TTC | CCC | TGC | AAT | ATC | ATC | TCC | CAG | ACC | CCG | AAT | GGA | AGG | 288 |

```
                Pro  Asn  Leu  Phe  Pro  Cys  Asn  Ile  Ile  Ser  Gln  Thr  Pro  Asn  Gly  Arg
                              85                         90                         95

TTT  ACT  CTG  GTC  ATG  CCG  CAT  CAG  CAT  CGC  AAC  TGC  AGC  TTC  TCC  ATC                    336
Phe  Thr  Leu  Val  Met  Pro  His  Gln  His  Arg  Asn  Cys  Ser  Phe  Ser  Ile
               100                      105                      110

ATT  TAT  CCT  GTA  GCG  ATC  AAA  ATA  TCC  GAT  CTC  ACC  CTG  GGA  CAC  TTA                    384
Ile  Tyr  Pro  Val  Ala  Ile  Lys  Ile  Ser  Asp  Leu  Thr  Leu  Gly  His  Leu
          115                      120                      125

AAT  GGT  CTG  CAG  TTA  AAG  AAG  TCC  TCC  GCA  GGC  TGT  GGG  GGA  ATA  GGA                    432
Asn  Gly  Leu  Gln  Leu  Lys  Lys  Ser  Ser  Ala  Gly  Cys  Gly  Gly  Ile  Gly
     130                      135                      140

GAC  TTT  GTG  GAG  CTG  CTG  GGA  GGA  ACT  GGT  TTG  GAC  CCT  TCC  AAG  ATG                    480
Asp  Phe  Val  Glu  Leu  Leu  Gly  Gly  Thr  Gly  Leu  Asp  Pro  Ser  Lys  Met
145                      150                      155                      160

CTG  CTT  TTA  GCT  GAT  CTC  TGC  TAC  CCT  TTA  CGT  GGC  CCA  GCC  CAG  ATG                    528
Leu  Leu  Leu  Ala  Asp  Leu  Cys  Tyr  Pro  Leu  Arg  Gly  Pro  Ala  Gln  Met
               165                      170                      175

AAA  GTT  GGC  TGT  GAC  CAC  ACG  GTA  CTG  CGC  ATG  GTC  TCC  AGT  GGA  AAA                    576
Lys  Val  Gly  Cys  Asp  His  Thr  Val  Leu  Arg  Met  Val  Ser  Ser  Gly  Lys
               180                      185                      190

CTC  TTA  AAT  CGT  GTG  ACT  TTT  GAG  TAT  CGA  AAG  CTG  GAA  CCA  TAT  GAG                    624
Leu  Leu  Asn  Arg  Val  Thr  Phe  Glu  Tyr  Arg  Lys  Leu  Glu  Pro  Tyr  Glu
          195                      200                      205

CTG  GAA  AAC  CCG  AAT  GGA  AAC  AGT  ATC  CAG  GAA  TTC  TGT  TTG  TCT  ACC                    672
Leu  Glu  Asn  Pro  Asn  Gly  Asn  Ser  Ile  Gln  Glu  Phe  Cys  Leu  Ser  Thr
     210                      215                      220

CTT  TGA                                                                                           678
Leu  .
225
```

( 2 ) INFORMATION FOR SEQ ID NO:6:

( i ) SEQUENCE CHARACTERISTICS:
        ( A ) LENGTH: 298 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:6:

```
Tyr  Leu  Glu  Leu  Arg  Glu  Ala  Ala  Asp  Tyr  Asp  Pro  Phe  Leu  Leu  Phe
1                   5                        10                       15

Ser  Ala  Asn  Leu  Lys  Arg  Asp  Val  Ala  Gly  Glu  Gln  Pro  Tyr  Arg  Arg
               20                       25                       30

Ala  Leu  Arg  Cys  Leu  Asp  Met  Leu  Ser  Leu  Gln  Gly  Gln  Phe  Thr  Phe
          35                       40                       45

Thr  Ala  Asp  Arg  Pro  Gln  Leu  His  Cys  Ala  Ala  Phe  Phe  Ile  Ser  Glu
     50                       55                       60

Pro  Glu  Glu  Phe  Ile  Thr  Ile  His  Tyr  Asp  Gln  Val  Ser  Ile  Asp  Cys
65                       70                       75                       80

Gln  Gly  Gly  Asp  Phe  Leu  Lys  Val  Phe  Asp  Gly  Trp  Ile  Leu  Lys  Gly
               85                       90                       95

Glu  Lys  Phe  Pro  Ser  Ser  Gln  Asp  His  Pro  Leu  Pro  Ser  Ala  Glu  Arg
          100                      105                      110

Tyr  Ile  Asp  Phe  Cys  Glu  Ser  Gly  Leu  Ser  Arg  Arg  Ser  Ile  Arg  Ser
     115                      120                      125

Ser  Gln  Asn  Val  Ala  Met  Ile  Phe  Phe  Arg  Val  His  Glu  Pro  Gly  Asn
     130                      135                      140

Gly  Phe  Thr  Leu  Thr  Ile  Lys  Thr  Asp  Pro  Asn  Leu  Phe  Pro  Cys  Asn
```

| 145 | | | | 150 | | | | 155 | | | | 160 | |
|---|---|---|---|---|---|---|---|---|---|---|---|---|---|
| Val | Ile | Ser | Gln | Thr 165 | Pro | Asn | Gly | Lys | Phe 170 | Thr | Leu | Val | Val | Pro 175 | His |
| Gln | His | Arg | Asn 180 | Cys | Ser | Phe | Ser | Ile 185 | Ile | Tyr | Pro | Val | Val 190 | Ile | Lys |
| Ile | Ser | Asp 195 | Leu | Thr | Leu | Gly | His 200 | Val | Asn | Gly | Leu | Gln 205 | Leu | Lys | Lys |
| Ser | Ser 210 | Ala | Gly | Cys | Glu | Gly 215 | Ile | Gly | Asp | Phe | Val 220 | Glu | Leu | Leu | Glu |
| Gly 225 | Thr | Gly | Leu | Asp | Pro 230 | Ser | Lys | Met | Thr | Pro 235 | Leu | Ala | Asp | Leu | Cys 240 |
| Tyr | Pro | Phe | His | Gly 245 | Pro | Ala | Gln | Met | Lys 250 | Val | Gly | Cys | Asp | Asn 255 | Thr |
| Val | Val | Arg | Met 260 | Val | Ser | Ser | Gly | Lys 265 | His | Val | Asn | Arg | Val 270 | Thr | Phe |
| Glu | Tyr | Arg 275 | Gln | Leu | Glu | Pro | Tyr 280 | Glu | Leu | Glu | Asn | Pro 285 | Asn | Gly | Asn |
| Ser | Ile 290 | Gly | Glu | Phe | Cys | Leu 295 | Ser | Gly | Leu | | | | | | |

BRAIN-DERIVED MEMBRANE-ASSOCIATED CRF BINDING PROTEINS

This invention was made with Government support under Grants DK-26741 and HD-13527 awarded by the National Institutes of Health. The Government has certain rights in the invention. The University of Reading and the Medical Research Council of Great Britain also contributed financially to this invention.

This invention relates generally to controlling the biological effect of Corticotropin releasing-factor (CRF) in mammals and more particularly to CRF binding proteins (CRF-BP) which are expressed on cell surfaces in the brain and have a high affinity for CRF.

BACKGROUND OF THE INVENTION

Stress is the demand placed upon an organism subjected to real or perceived threat or challenge. In order to maintain homeostasis, the organism mounts an array of hormonal, autonomic and behavioral responses, some of which are common to most stressful circumstances, such as activation of the pituitary adrenal axis and sympathetic nervous system and behavioral arousal. The stress response in large part is regulated through Corticotropin-Releasing Factor (CRF), a 41-residue hypothalamic peptide that stimulates the secretion and biosynthesis of pituitary ACTH, leading to increased adrenal glucocorticoid production. This process is regulated through a negative feedback loop whereby glucocorticoids suppress CRF production.

Although originally isolated and characterized on the basis of its role in this hypothalamopituitary-adrenal (HPA) axis, CRF has been found to be distributed broadly within the central nervous system as well as in extraneural tissues, such as the adrenal glands and testes, where it may also act as a paracrine regulator or a neurotransmitter. Moreover, the involvement of CRF in affective disorders, such as depression and anorexia nervosa, and in modulating reproduction and immune responses suggests that changes in CRF expression may have important physiological consequences. For example, perturbations in the regulatory loops comprising the HPA axis often produce chronically elevated levels of circulating glucocorticoids; such patients display the physical hallmarks of Cushing's syndrome, including truncal obesity, muscle-wasting, and reduced fertility. Most cases of Cushing's syndrome are caused by ACTH-producing tumors of the pituitary or, less frequently, nonendocrine tissue. Adrenal gland tumors or ectopic adrenal tissue account for 10–30% of occurrences of the disorder, but, in contrast to the pituitary-dependent form, plasma ACTH levels are not elevated. Several patients with Cushing's syndrome have been reported with ectopic CRF-secreting tumors, leading to the proposal that CRF can chronically drive pituitary ACTH production and, in turn, glucocorticoid release. It has been suggested that excess production of CRF may cause pituitary hyperplasia, leading to microadenoma formation and excess ACTH production. That pituitary hyperplasia accompanies some CRF-secreting tumors is consistent with this proposal.

CRF is thus a very potent stimulator of the synthesis and secretion of various peptides in the human body. The rat and human species have the same CRF molecule (r/h CRF or hCRF), which is a 41-residue peptide having the structure which is set forth in U.S. Pat. No. 4,489,163. Ovine CRF (oCRF) was first characterized, and its 41-residue structure is set forth in U.S. Pat. No. 4,415,558.

Although CRF levels in human peripheral circulation are normally low, there are often elevated levels of CRF in the maternal circulation, which levels progressively increase throughout pregnancy. It has been found that the increasing concentrations of CRF in pathological cases of pregnancy, such as pregnancy-induced hypertension and pre-term labor, are substantially and significantly elevated above those found in normal pregnancies (Campbell et al., *J. Clin. Endocr. & Metab.*, 64:1054–1059, 1987).

It is believed that this maternal plasma CRF most likely originates from the placenta wherein it plays a paracrine role. Placenta cells have been shown to respond to CRF and to produce CRF and its mRNA. Even though CRF concentrations measured in late gestational maternal plasma are similar to levels reported in rat hypothalamic portal blood, which levels are capable of stimulating ACTH release in vitro, it does not appear that there is normally overproduction of ACTH during pregnancy. However, maternal plasma ACTH concentrations do increase slightly with advancing gestation.

A number of workers have used molecular crosslinking with radioiodinated CRF to identify putative ovine CRF binding proteins and receptors in brain, pituitary and AtT-20 cells which range from 40–70 kD in molecular weight. After subtraction of the molecular weight of the cross-linked CRF (~5 kD), the main protein form that was found in the pituitary gland was reported to be 70 kD, Nishimura et al., *J. Biol. Chem.*, 262, 12893 (1987). A lower molecular weight protein of about 50 kD was reported to be the major brain form; Grigoriadis, et al., *Endocrinology*, 125, 3068–3077 (1989). The heterogeneity in sizes of these proteins was thought to be possibly due to differential glycosylation because, after N-glycanase treatment, only one cross-linked species of about 40–46 kD was observed in both brain and pituitary.

There were also reports of proteins in human plasma which are capable of biologically inactivating CRF, see Linton, E. A., et al. *Clin. Endo.* 28, 315–324 (1988) and Behan, D. P., et al. *J. Endo.* 122, 23–31 (1989), the latter of which discloses a partial purification process which resulted in an isolate that has now been determined to have been no more than about 50% pure. The purification of the isolated protein was ultimately accomplished, and sequencing of the pure compound provided sufficient amino acid sequence information to clone the DNA encoding this protein, which is now referred to as human serum hCRF-binding protein (hCRF-BP) [SEQ ID NO:6], E. Potter, et al., *Nature*, 349, 423–426 (Jan. 31, 1991). It has been proposed that the role of this protein substance might be the prevention of inappropriate pituitary-adrenal stimulation during pregnancy, and recombinant rat and human serum CRF-BPs have now been expressed in COS cells. They have been found to bind to the 41-residue CRF with high affinity, so as to be capable of therapeutically modulating the effect of CRF.

Some additional preliminary work has been done trying to isolate CRF receptors. Grigoriadis and DeSouza, *J. Biol. Chem.*, 263, 10927–10931 (1988) and Grigoriadis, et al., supra, speculated that the molecular weight of the brain CRF receptor to be about 58 kD, less the MW of ovine CRF; however, their characterizations have been limited to estimates of the molecular weight of this protein by SDS-PAGE analysis of covalent complexes formed by chemical crosslinking between the receptor and $^{125}$I-CRF which are present within crude extracts containing a myriad of other proteins. They have not published more definitive information with regard to the CRF receptors and thus have not enabled others to determine or utilize the receptor structures.

Synaptic membrane CRF binding sites in the mammalian brain are integral to central relays for several sensory modalities including the olfactory bulb which comprises prominent sites of CRF-BP gene expression. The presence of membrane-associated CRF receptors in the mammalian brain are demonstrated inter alia by the presence of binding proteins in important cell groups which mask the immunodetection of CRF peptides present for the regulation of corticotropin production and intercellular communication of the central nervous system. Present studies in this field are aimed at determining how the expression of membrane-associated brain CRF-BPs are regulated by stress and corticosteroid influences.

In order to study the structure and biological characteristics of brain-derived membrane-associated proteins which bind to CRF and also to study the role played by these binding proteins in the responses of various cell populations to CRF stimulation, or to use them effectively in therapy, as components in affinity columns, diagnosis or assay, homogeneous compositions of the binding proteins are needed. Such compositions are theoretically available via purification of solubilized proteins expressed by cultured cells; however, even in cell lines known to express detectable levels of CRF receptors, such is present as a very minor component of total cellular proteins. It is therefore desirable that the nature and the structure of such membrane-associated CRF binding proteins be ascertained so that these proteins can be provided in sufficient quantity to allow them to be utilized for screening of compounds for drug design, for therapy by modulation of transactivation of CRF receptors by means of competition for tissue binding sites, for affinity columns and for other appropriate purposes.

SUMMARY OF THE INVENTION

Several membrane-associated CRF-BP proteins have now been isolated from sheep (ovine) brain and characterized; they exhibit an ability to bind to hCRF which has been immobilized on a solid-phase matrix. Proteins of molecular weights of about 33 and about 35 kD have been obtained; each binds to $^{125}$I-radiolabeled human CRF and to ovine CRF and can be cross-linked thereto using a bifunctional cross-linking agent, such as disuccinimidyl suberate, if desired. Biologically active, naturally occurring proteolytic products of the 35 kD ovine brain-derived membrane-associated CRF-BP have also been identified as the N-terminal fragments of the 35 kD protein which are active in complexing with the 33kD CRF-BP and in causing the in vivo dissociation of a 33kD/35kD protein complex. An N-terminal fragment of hCRF-BP (SEQ ID NO:6) is similarly biologically active to cause dissociation of complexes of membrane-associated CRF-BPs. Biologically active CRF binding protein counterparts of the 35 and 33 KD ovine proteins have also been identified which have a deletion of an internal amino acid sequence that is believed to be the result of alterative gene splicing.

The present invention particularly provides mammalian, brain-derived, membrane-associated CRF binding proteins, including human homologs, which can be employed to complex with CRF and thereby modulate CRF actions in mammals by means of antagonistic association and which can also be employed for the design of more effective analogs and drugs. The peptides of the present invention are also useful for screening compounds in competitive binding assays in order to determine their relative affinities for CRF receptors and the like. These peptides are also useful for coupling to affinity column matrices for the purification of CRF from biological samples.

DETAILED DESCRIPTION OF PREFERRED EMBODIMENTS

CRF stimulates the biosynthesis and secretion of ACTH and β-endorphin-like immunoactivities (β-END-LI) through a plasma membrane receptor protein which functions in combination with membrane-associated binding proteins described herein. The proteins disclosed herein include but are not limited to those isolated from ovine brain. Biologically active analogs can be readily constructed by those skilled in the art once the amino acid sequence is known.

Unless defined otherwise, all technical and scientific terms used herein have the same meaning as is commonly understood by one of skill in the art to which this invention belongs. The amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

The term homology is used in its usual and well known sense of indicating correspondence between members in a sequence, e.g. either on an amino acid (AA) level or at the nucleotide level. For purposes of this application, by homologous is meant having at least about 70% correspondence, by substantially homologous is meant having a correspondence of at least about 80%, and by highly homologous is meant having a correspondence of at least about 90% or preferably about 95% or higher.

Polypeptide and peptide designates a linear series of amino acid residues connected one to the other by peptide bonds between the alpha-amino and alpha-carboxy groups of adjacent residues. The term polypeptide is used somewhat interchangeably with peptide but, unless otherwise limited, is generally also used to include the proteins described herein.

The term "analog" includes any polypeptide having an amino acid residue sequence substantially identical to a sequence specifically shown herein in which one or more residues have been conservatively substituted with a functionally similar residue and which displays the ability to mimic CRF-BP as described herein. Examples of conservative substitutions include: the substitution of one non-polar (hydrophobic) residue, such as isoleucine, valine, alanine, glycine, leucine or methionine for another; the substitution of one polar (hydrophilic) residue for another, such as arginine for lysine, glutamine for asparagine, threonine for serine; the substitution of one basic residue such as lysine, arginine or histidine for another; and the substitution of one acidic residue, such as aspartic acid or glutamic acid for the other. The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to from O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues relative to the sequence of a polypeptide whose sequence is shown herein, so long as the requisite biological activity is maintained.

As used herein, the terms "pharmaceutically acceptable", "physiologically tolerable" and grammatical variations thereof, as they refer to compositions, carriers, diluents and reagents, are used interchangeably and represent that the materials are capable of administration to a mammal without the production of undesirable physiological effects such as nausea, dizziness, gastric upset and the like.

The term "homolog" used herein refers to analogous proteins, peptides and DNA sequences from heterologous mammalian species that have evolved insignificant changes but perform the same biological function in substantially the same way.

The term "biologically active fragment" as used herein refers to fragments of the disclosed proteins or peptides which have been truncated with respect to either the N- or C-termini, or both; or the 5' or 3' end, or both, of the corresponding DNA coding regions, which fragments perform substantially the same or a directly related function or encode peptides which perform substantially the same or a directly related function as the precursor.

"Modulating the transactivation of CRF receptors or modulating the action of CRF in mammals" as used herein comprises administering a therapeutically effective amount of a physiologically tolerable composition containing a brain-derived CRF-BP protein or biologically active fragment or homolog thereof to complex with CRF and/or dissociate CRF-BP/CRF-BP complexes and thereby modulate CRF actions in mammals by means of direct or induced antagonistic (competitive) association with endogenous CRF thus lowering the ambient in vivo concentration of CRF.

CRF binding proteins obtained from detergent solutions of sheep and rat brain cells were isolated with full retention of CRF binding activity. To obtain these binding protein molecules, mammalian brains were appropriately homogenized, treated, extracted and the isolated CRF-BPs were characterized. It is convenient to process groups of 3 sheep brains per isolation, as described in detail hereinafter in Example I.

Ovine CRF-BPs of 33 kD and 35 kD were purified from sheep brain as described in Example I and individually tested. CRF-binding protein-like immunoreactivity was detected in these 2 bands using a CRF-BP ligand immunoradiometric assay (LIRMA) as set forth in Example I. To demonstrate their affinities for CRF, the isolated brain ovine CRF-BP proteins are each cross-linked to either oCRF or hCRF using disuccinimidyl suberate as a bifunctional cross-linking agent. Each is found to bind to $^{125}$I-radiolabeled hCRF and oCRF. To further characterize these isolated proteins, binding assay experiments, as well known in the art, are also carried out with the purified membrane-associated CRF-BP proteins to determine the affinity at which they bind to CRF. The results of these assays are expressed in terms of the dissociation constant $K_D$, which is equal to the reciprocal of the concentration of free CRF at the equilibrium point where one-half of the CRF-BP present is bound to, i.e. complexed with, CRF. In other words, when the binding protein has a high affinity and binds CRF strongly, a low CRF concentration will half-saturate the total amount of binding protein molecules. Generally, a dissociation constant of about 5 or lower is considered to be an indication of strong affinity, and a $K_D$ of about 6 to 14 is an indication of intermediate affinity. The 33 kD molecule binds hCRF with strong affinity having a $K_D$ =0.25±0.2 nanomolar. The 35 kD membrane-associated binding protein, which is an N-terminally extended version of the 33 kD protein, has a $K_D$ =7.5±2.5 nM. Accordingly, slightly shorter membrane-associated binding proteins than the 33 kD protein are considered to also have similar strong binding affinities. Furthermore, the isolated ovine CRF-BPs are found to be specifically competed with cold CRF at a concentration of about 1 µM, showing that these proteins are indeed selectively complexing with the 41-residue CRF molecule.

These membrane-associated CRF-BPs, including those which bind to CRF with an intermediate affinity, e.g. between about 6 and about 15 nanomolar, are particularly useful in promoting the delivery of CRF to the cell surface receptors where its biological activity comes to fruition. Because both of these isolated ovine brain binding proteins bind to CRF, it is clear that binding proteins having N-termini intermediate therebetween would exhibit generally similar binding affinity. Moreover, it is considered that binding proteins further shortened from the N-terminus of the 33 kD protein by the elimination of one or a sequence of residues would also exhibit intermediate binding affinity.

As described hereinafter in detail, the 35 kD protein was found to have the 295 AA sequence set forth in SEQ ID NO:1 following a series of different experimental procedures.

N-terminal Edman degradation was individually performed on the two isolated brain ovine CRF-BPs by applying each of the isolated proteins to gas phase sequence analysis after SDS-PAGE and elctrotransfer to a PUDF membrane. N-terminal sequence analysis of the 35 kD band revealed a protein containing the N-terminal amino acid (AA) sequence: Glu-Ala-Val-Asp-His-Asp-Ser-Phe-Pro-His-Leu-Ala-Gly-Gly-Ala-Ser (residues 1–16 of SEQ ID NO:1). N-terminal sequence analysis revealed the 33 kD band to contain a protein containing the N-terminal amino acid (AA) sequence:

Glu-Leu-Glu-Gly-Glu-Pro-Leu-Tyr-Arg-Arg-Ala-Leu-Arg-Cys-Val-Asp-Met-Leu (residues 20–37 of SEQ ID NO:1).

Tryptic digestion of these purified proteins, followed by purification of the tryptic fragments, was also carried out. There were fragments among the tryptic fragments of the 35 kD protein which corresponded to all of the purified tryptic fragments of the 33 kD protein.

N-terminal sequence analysis was then carried out on these tryptic fragments and resulted in identification of the following N-terminal AA sequences:

Phe-Pro-Ser-Ser-Gln-Asp-His-Pro-Leu-Pro-Thr (residues 96–106, of SEQ ID NO:1);

Tyr-Val-Asp-Phe-Cys-Asp-Ser-Gly-Leu-Ser-Arg (residues 110–120 of SEQ ID NO:1);

Ser-Ser-Ala-Gly-Cys-Gly-Gly-Ile-Gly-Asp-Phe-Val-Glu-Leu-Leu-Gly-Gly (residues 206–222 of SEQ ID NO:1);

Val-Gly-Cys-Asp-His-Thr-Val-Leu-Arg (residues 248–256 of SEQ ID NO:1); and

Val-Thr-Phe-Glu-Tyr-Arg (residues 267–272 of SEQ ID NO:1). The presence of the Cys residues was deduced from the totality of experimental information obtained.

Following the purification and characterization of the 33 and 35 kD brain-derived ovine CRF-BPs by identification of multiple AA sequences, synthetic 5' sense and 3' antisense oligonucleotides directed to separate presumed DNA coding regions were used to clone ovine CRF-BP gene fragments by means of Polymerase Chain Reaction (PCR) from sheep cDNA (derived from sheep brain mRNA). Two ovine CRF-BP cDNA coding region clones of 552 and 441 base pairs (bp) are obtained as set forth herein as SEQ ID NO:3 and SEQ ID NO:4, respectively. In addition, a labelled CRF-BP cDNA coding region was then used as a molecular hybridization probe to obtain a gene segment from a lambda Zap™ (Stratagene, La Jolla, Calif.) cDNA library made from ovine brain mRNA. The probe was successful in identifying a 678 bp ovine CRF-BP partial gene cDNA segment (SEQ ID NO:5) in the sheep brain cDNA library.

Subsequent comparison of the corresponding amino acid sequences from the Edman degradation N-terminal sequence analyses, the PCR-cloned cDNA coding regions, and the partial cDNA coding region yields a composite amino acid sequence of the 35 kD ovine CRF-BP (SEQ ID NO:1) and of the 33 kD ovine CRF-BP (residues 20–295 of SEQ ID NO:1). By comparison of the 2 PCR-cloned segments, it is deduced that there is a protein (SEQ ID NO:2) having a deletion of 37 AA residues corresponding to the 35 kD ovine CRF-BP and also a protein (residues 20–258 of SEQ ID NO:2) corresponding to the 33 kD ovine CRF-BP. Also deduced is the biologically active N-terminal, 18 or 19 AA residue, proteolytic cleavage product of the 35 kD ovine CRF-BP (residues 1–18 or 1–19 of SEQ ID NO:1). There are human membrane-associated CRF-BP proteins of about 33 kD and about 35 kD in the human brain, which are homologous to the ovine CRF-BPs, as there also are in rat brain.

The 35 kD ovine protein from brain has some sequences in common with the C-terminal portion soluble human serum CRF-BP (SEQ ID NO:6), which has now been expressed recombinantly. It has been determined that the mature human serum CRF-BP contains 5 disulfide bridges located linearly throughout the molecule, respectively between $Cys^{36}$ and $Cys^{57}$, $Cys^{80}$ and $Cys^{117}$; $Cys^{159}$ and $Cys^{181}$, $Cys^{213}$ and $Cys^{240}$, and $Cys^{253}$ and $Cys^{294}$ in SEQ ID NO:6. It is considered that a similar linkage pattern exists in the ovine purified proteins. In ovine brain-derived CRF-BP having the 37 AA deletion, at least one cysteine-cysteine potential loop is missing, which would cause the tertiary structure of such brain CRF-BP to be substantially different from that of the isolated 35 kD ovine brain protein and the secreted serum form of the human CRF-BP. Moreover, the very substantial structural differences in the region of the N-terminus of the brain-derived CRF-BPs from the structure of the soluble serum CRF-BP proteins are believed to contribute to their association with neuro-membranes and their function in the brain.

The ovine CRF-BP mRNA internal deletion represented by the cDNA PCR clone (SEQ ID NO:4) and the composite amino acid sequence (SEQ ID NO:2) is believed to be a result of alternate mRNA splicing. This results in the loss of the first disulfide loop in secondary structure and demonstrates the diversity of CRF-BPs as herein disclosed.

The 33 kD brain-derived ovine CRF-BP which lacks the 19-amino acid N-terminal domain represents 70% of the ovine brain-derived membrane-associated CRF-BP in vivo and binds CRF with high affinity as described supra. This 33 kD membrane-associated CRF-BP also has been demonstrated to physically complex with the 35 kD membrane-associated CRF-BP, and it is believed that this complexing is via the 19-residue N-terminus of the larger biomolecule. During the biological existence of this 33kD/35kD CRF-BP complex in vivo, the high affinity CRF binding sites of both complexed CRF-BPs are unavailable or of substantially lesser binding affinity. This results in an in vivo relative increase in ambient CRF which is free to bind synaptic sites. Furthermore, the 19residue N-terminal proteolytic cleavage product of the 35 kD CRF-BP is biologically active to dissociate the 33kD/35kD CRF-BP complex, thus freeing the high affinity CRF binding sites, the result of which reduces the level of CRF available to bind synaptic receptors. Therefore, this peptide is considered therapeutically valuable in its ability to decrease the level of CRF available in the brain. Homolog versions of this peptide are present in other mammalian species, including humans where the N-terminal sequence of SEQ ID NO:6, e.g. residues 1–21, is considered to exert a similar biological function. The 18 and 19 residue N-termini of the 35 kD ovine brain-derived membrane-associated CRF-BP (residues 1–18 and 1–19 of SEQ ID NO:1) are also medically valuable for the design of chemical derivatives, analogs and comprehensive pharmaceutical compound designs. It is considered that this described family of compounds may be used to direct the activity of CRF to the vicinity of specific organs. The peptides/compounds are medically perceived to provide valuable therapeutics, for instance, in the treatment of local inflammation.

Naturally occurring CRF-BP proteins constitute only minor constituents of normal mammalian membranes, being present in only very impure form in extracts of such membranes, relative to other native proteins also present. Because of the work involved, the limited availability of biological samples, and the relatively low concentration in mammalian brain, it would be impractical to prepare CRF-BP by purification from natural sources. Therefore, brain-derived membrane-associated CRF-BPs are not practically available for clinical use or in the comprehensive design of analogous pharmaceutical compounds unless recombinant DNA production of the proteins and/or analogs are enabled, which of course entails knowing the entire amino acid structure of the native proteins as disclosed herein.

CRF-BP polypeptide fragments can be synthesized by any of the techniques that are known to those skilled in the polypeptide art, including recombinant DNA techniques. Synthetic chemistry techniques, such as solid-phase Merrifield-type synthesis, are also preferred for producing polypeptide fragments for reasons of purity, antigenic specificity, freedom from undesired side products, ease of production and the like.

Recombinant DNA techniques, for example, can be used to generate organisms or cell lines that produce the heterologous protein in significantly higher proportions, relative to total protein, in the cellular material and/or the secretions thereof; as compared to the proportions at which native CRF-BPs are present. Construction of synthetic genes which encode the ovine CRF-BPs, as well as other mammalian CRF-BPs, and therefore recombinant expression of these proteins is made feasible by the amino acid sequences disclosed herein. Because the starting material from which such synthetic recombinant CRF-BP proteins are isolated is from media which is essentially free of protein contaminants and has a substantially greater concentration of the heterologous protein, available purification techniques can fairly simply produce more highly purified CRF-BP preparations in relatively copious amounts. For example, expression of a synthetic DNA coding region corresponding to the amino acid sequence SEQ ID NO:1 in CHO cells can be effected using standard techniques to produce the 295-residue glycosylated protein. An exemplary recombinant production is described in Example IV. As a result, methods of treatment can be carried out by the administration of the recombinant proteins and their effective analogs. Examples of proteins and peptides which are advantageously employed include the 35 kD ovine CRF-BP (SEQ ID NO:1); the 33 kD ovine CRF-BP (residues 20–295 of SEQ ID NO:1; these two proteins with the 37 amino acid deletion (SEQ ID NO:2 and residues 20–258 of SEQ ID NO:2); N-terminal fragments of the mature 35 kD protein (SEQ ID NO:1), for example residues 1–18 or 1–19 (beginning with Glu and ending with Lys or Arg); and N-terminal fragments of the mature human serum protein (for example residues 1–21 of SEQ ID NO:6).

Pharmaceutical compositions will usually contain the peptides in conjunction with a conventional, pharmaceutically-acceptable carrier. For treatment, substantially pure isolated or synthetic CRF-BP or a nontoxic salt thereof, combined with a pharmaceutically acceptable carrier to form a pharmaceutical composition, is preferably administered parenterally to mammals, including humans, either intravenously (IV), subcutaneously, intramuscularly, percutaneously, e.g. intranasally, or introcerebroventricularly; oral administration is possible with an appropriate carrier.

Any polypeptide of the present invention may be used in the form of a pharmaceutically acceptable salt. Suitable acids which are capable of forming salts with the peptides of the present invention include inorganic and organic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di-, and tri-alkyl and -aryl amines (e.g., triethylamine, diisopropyl amine, methyl amine, dimethyl amine and the like) and optionally substituted ethanolamines (e.g., ethanolamine, diethanolamine, and the like).

Therapeutic compositions of the present invention may desirably contain a physiologically tolerable carrier together with a brain-derived CRF-BP protein, human homolog, polypeptide fragment or biologically active analog as described herein, dissolved or dispersed therein as an active ingredient. In a preferred embodiment, the therapeutic composition is not immunogenic when administered to a mammal or a human patient for therapeutic purposes.

The preparation of a pharmacological composition that contains active ingredients dissolved or dispersed therein is well understood in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein which salts were hereinbefore described.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

Administration of these CRF-BPs or certain polypeptide fragments thereof is effective to reduce high ACTH levels in mammals caused by excessive CRF, which is referred to herein as "CRF-induced ACTH release." In this manner, the CRF-BPs are useful in treating high cortisol (i.e., glucocorticoids) levels which are associated with hypercortisolemia, Cushing's Disease, alcoholism, anorexia nervosa and similar diseases. The CRF-BP proteins and fragments thereof are also useful to treat abnormalities which occur during the later stages of pregnancies; for example, they can be used to reduce pregnancy-induced complications and increased CRF levels which can otherwise result in excessive release of ACTH. In addition, CRF-BP proteins or fragments thereof can be administered to reduce the ratio of CRF/CRF-BP present in a patient. The IV administration of CRF-BPs may also be employed in certain instances to modulate blood pressure and thereby combat hypotension. The CRF-BP proteins can be effectively used to modulate the action of CRF on the brain, particularly with respect to control of appetite, reproduction, growth, anxiety, depression, fever and metabolism, as well as the regulation of blood pressure, heart rate and blood flow. As previously indicated, the short N-terminal fragments are also expected to be valuable in the brain.

Thus, the present invention provides for a method for modulating the action of CRF in mammals comprising administering a therapeutically effective amount of a physiologically tolerable composition containing a CRF-BP protein or polypeptide fragment of the present invention. A therapeutically effective amount is an amount calculated to achieve the desired effect, i.e., to decrease the amount of ACTH or decrease the CRF/CRF-BP ratio in a patient. The required dosage will vary with the particular treatment and with the duration of desired treatment. Very generally, daily dosages of between about 10 micrograms and about 1 milligram per Kg of body weight are presently contemplated, dependent however on the size of the protein or polypeptide, i.e. a relatively lesser amount might be employed of the short N-terminal fragments. In addition, changes in ACTH levels can be monitored during a treatment regimen to determine the effectiveness of the administered CRF-BP protein or polypeptide fragment over time. The level of ACTH present in a patient, can be readily determined by routine clinical analysis, and assays to monitor the level of ACTH are well known. Thus, the present therapeutic method also provides a way to decrease ACTH levels in a human patient.

Preparations of purified, isolated membrane-associated CRF-BP or recombinant protein are advantageously employed to inhibit CRF-induced ACTH release in vivo. Thus, these CRF-BPs can be administered therapeutically to bind to and inactivate CRF thereby reducing high ACTH levels in mammals caused by excess CRF. Moreover, they can be used to reduce pituitary ACTH secretion and hence reduce cortisol levels under any condition in which they are abnormally high, such as during chronic stress or in patients afflicted with anorexia nervosa or alcoholism. It has been found that CRF-BPs when administered intravenously (IV) have also proved effective to prevent CRF-induced ACTH release. Furthermore, it is considered that IV administration of the CRF-BPs can be used to raise blood pressure and in this manner combat hypotension.

These binding proteins can also be used in assay systems to monitor the effects of chemical modifications to CRF on its binding affinity, and they are useful for screening compounds in competitive binding assays and in assays useful to determine affinities for CRF receptors. Representative assays are disclosed in U.S. Pat. application Ser. No. 08/097,828, filed Jul. 23, 1993, which is commonly assigned, the disclosure of which is incorporated herein by reference.

Methods of screening compounds for the therapeutically valuable property of the ability to cause in vivo dissociation of CRF-BP/CRF-BP complexes, e.g., the property to cause dissociation of the brain-derived 33 kD/35 kD or possibly of the 33 kD/N-terminal cleavage peptide complexes are herein enabled. For example, equimolar amounts of the ovine brain-derived 33 kD CRF-BP and 35 kD CRF-BP and an excess of radiolabelled CRF are mixed in an approximate physiological ionic and buffered solution. Then, after biological equilibrium is achieved, the putative therapeutic compound, i.e., a small peptide, or nonpeptide e.g., asteroid, is introduced into the solution to test whether dissociation occurs, thereby freeing the 35 kD CRF-BP and allowing it to bind CRF. Subsequent to kinetic equilibrium of the biological solution, purified antibody directed toward the N-terminus of the 35 kD CRF-BP is added. Upon re-equilibration under physiological conditions, the first antibody is precipitated with a second conjugate antibody or Staphlococcus protein A. In the case of the N-terminal peptides described supra or an effective drug candidate, the 35 kD CRF-BP/labelled CRF complex is thereby precipitated. Quantitative analysis is performed and compared by scintillation counting to determine the relative effectiveness of the putative therapeutic compound.

These CRF-binding proteins when coupled to a solid matrix can be used to isolate CRF from biological samples or from aqueous solution as a part of an affinity column or the like. The binding ability of these CRF-BPs allows them to be used in affinity chromatography to purify hCRF or homologs of CRF. These CRF binding proteins can be coupled to Sepharose or other suitable affinity chromatography supports and used to purify CRF and CRF analogs from solutions and biological samples.

The following examples describe certain of the experimental procedures which were employed and to which reference was variously made hereinbefore.

EXAMPLE I

To obtain the purified proteins which bind to CRF, three sheep brains were homogenized in 700 ml of standard binding buffer containing 50 mM sodium phosphate, 100 mM sodium chloride, 25 mM EDTA, 0.1 volume percent sodium azide (SPEA) containing 10 mM magnesium chloride, 2 mM phenylmethyl-sulfonylfluoride (PMSF), 2.8 µg/ml leupeptin and 7 µg/ml aprotinin. The homogenate was divided into 500 ml centrifuge buckets and spun at 3000 rpm for 10 minutes in a centrifuge to separate nuclei and particulate matter. The supernatant was decanted, and the pellet was solubilized by the addition of an aqueous solution of NP-40 liquid detergent at a concentration of about 0.2% by volume and by stirring at 4° C. for 1 hour. NP-40 (Nonidet P-40) is a detergent consisting of an octylphenol-ethylene oxide condensate containing an average of nine moles of ethylene oxide per mole of phenol; it is available from a number of suppliers, including Fluka Chemical Corporation and Sigma Chemical Company. The NP-40 employed was a >99% pure substance obtained from Fluka Chemika-Bio-Chemika, Ronkonkoma, N.Y., 11779. The mixture was then recentrifuged at 5000×g for 15 minutes at 4° C., and the supernatant was decanted. The resultant pellet was re-extracted by the addition of 400 ml of binding buffer, and the mixture was recentrifuged as described above without the addition of NP-40. The re-extraction procedure was repeated four times. All the resulting supernatants were pooled and then diluted to a final volume of 4 L with binding buffer.

1 ml of granular Affigel chromatographic media (BioRad) was washed with 50 ml of distilled water at 4° C. 1 mg of CRF was then dissolved in 7 ml of coupling buffer which was 100 mM Hepes, pH 7.4. The Affigel media was added to the mixture, and the container was rotated overnight at 4° C., allowing the CRF peptide to couple to the media in a total volume of 10 ml. The solid phase was then left to settle under gravity, and the supernatant was decanted. Unreacted groups on the Affigel media were then blocked by exposing the solid phase to 1M ethanolamine/HCL pH 8.0 and rotating in a suitable container for 1 hour at 25° C. The resulting CRF-solid phase conjugate was transferred to a sintered glass funnel and washed sequentially with ten 50 ml batches each containing 50 mM sodium acetate/formate/20% acetonitrile buffer, pH 3.0 and 100 mM Hepes pH 7.4. The CRF-solid phase conjugate was then finally diluted by thoroughly mixing with 9 mls of cold, unactivated granular Sepharose 4B, and this dilute mixture was used as the media for the 1st step of the affinity chromatographic separation.

Media for a 2nd step separation was prepared as described above except that no dilution with cold unactivated Sepharose 4B was used, so that the 1 ml of granular Affigel-CRF conjugate alone was employed to treat the much smaller volume of material.

The 4 liters of extract was then exposed to the 10 ml of diluted CRF-solid phase conjugate by stirring this chromatographic media with the extract overnight at 4° C. After exposure, the solid phase was recovered by filtering the 4 L extract through a coarse 600 ml sintered glass funnel. The solid phase was then washed off the sintered glass with 0.9% NaCl and transferred to a BioRad Econo column (20×2.5 cm) where it was further washed with approximately 200 mls of 0.9% NaCl. The bound proteins were then desorbed with 50 mL of elution buffer, i.e. 80% 50 mM sodium acetate-formate buffer/20% acetonitrile, pH 3.0, containing 0.1% by volume bovine serum albumin (BSA); ten 5 ml fractions were sequentially collected throughout this elution.

Each of the fractions was assayed for CRF-BP-like immunoreactivity with the aid of a CRF-BP ligand immunoradiometric assay (LIRMA) which utilized an antibody (Ab 5144) raised against the entire human recombinant mature protein hCRF-BP(1-298). The assay utilized CRF-BP antibody 5144 at 1:1000 initial dilution, and a high affinity radiolabeled $^{125}$I-hCRF trace [50,000 c.p.m.]. 50µl of radio-iodinated CRF trace [diluted to 50,000 c.p.m./50 µl in assay buffer]is added to a silicate glass tube containing an aliquot from each fraction followed by incubation for 30 minutes at room temperature to allow binding to occur. CRF-BP antibody 5144, i.e. 50 μl diluted 1:1000 in assay buffer (SPEA containing 0.25% B.S.A. and 10 mM $MgCl_2$), is then added to each glass tube and incubated for a further 30 minutes at room temperature. If desired to obtain competitive binding curves as a part of an assay of this type, binding is allowed to occur in the presence of a series of cold CRF concentrations ranging from 0 to 1000 nM. Bound complexes are then precipitated by the addition of 200 μl of precipitated sheep anti-rabbit [SAR]second antibody [a mixture containing SAR1: 20, 1% NRS, 4% PEG, 50 mM sodium phosphate, 0.1% sodium azide], followed by incubation for 30 minutes at room temperature. The antibody-bound-$^{125}$I-CRF precipitate is then separated by centrifugation [3000×g]at 4° C. for 20 minutes, and the resulting pellets are counted in a gamma counter.

Active fractions were then pooled, and the pH was adjusted to about 7.5 with 1M tris base, providing approximately 15 ml of eluant. This eluant was then percolated at 4° C. 5 times over the undiluted CRF-solid phase conjugate which had been loaded into a BioRad Econo column (0.7×10 cm). The solid phase conjugate column was then washed sequentially with 40 mls of 0.9% NaCl and 15 mls of 80% 50 mM sodium acetate-formate/20% acetonitrile buffer, pH 6.8. Bound proteins were then finally eluted in five 0.5 ml fractions using the same elution buffer which was used in eluting the proteins from the first affinity chromatography step but without including any BSA.

The active fractions which eluted from this solid phase column and which bound to Ab 5144, as determined by LIRMA, were pooled and then concentrated to approximately 100 μl under vacuum in a Speed-Vac™ concentrator. These concentrates were then reduced by the addition of SDS sample buffer containing 5% mercaptoethanol in an amount of about 4 times their volume, and the pH was adjusted to approximately neutral by the addition of 5M NaOH, dropwise, until the sample buffer color changed from yellow to pale blue. The concentrates were then subjected to SDS electrophoresis on 10% SDS polyacrylamide gels for 4 hours at 25° C. The separated proteins were then transferred onto Immobilon-P blotting membrane by performing horizontal electrophoresis for 45 minutes at 25° C. in a BioRad transblot apparatus, utilizing 100 mM 3-[cyclohexylamino] -1-propanesulfonic acid (CAPS), pH 11, buffer containing 10% methanol as the transfer buffer. Protein bands were then visualized by staining the Immobilon membrane with Amido black staining solution for 5 minutes at room temperature.

Prominent bands were observed corresponding to 33 and 35 kD. Stained protein bands were then cut out from the Immobilon membrane, which is a polyvinylidene fluoride (PVDF) membrane, and they were stored until use in Eppendorf tubes containing 1 ml of distilled water which are frozen at −70° C. The procedure as described in this example is repeated using 2 more groups of three sheep brains each, and a similar staining pattern is obtained each time on the Immobilon membrane.

The procedure as described is repeated using groups of 500 rat brains each, and a similar staining pattern is obtained each time on the Immobilon membrane. Similar results are obtained using human brain tissue.

EXAMPLE II

The two isolated 35 kD and 33 kD brain-derived membrane-associated ovine CRF-BPs from Example I were characterized by determining amino acid sequence data in the following manner.

N-terminal Edman degradation was individually performed on the isolated brain ovine CRF-BPs by applying each of the isolated proteins to gas phase sequence analysis after SDS-PAGE and electrotransfer to a PUDF membrane. N-terminal sequence analysis of the 35 kD ovine CRF-BP revealed a protein containing the N-terminal amino acid (AA) sequence: Glu-Ala-Val-Asp-His-Asp-Ser-Phe-Pro-His-Leu-Ala-Gly-Gly-Ala-Ser (residues 1–16 SEQ ID NO:1). N-terminal sequence analysis revealed the isolated 33 kD ovine CRF-BP to contain a protein containing the N-terminal amino acid (AA) sequence:

Glu-Leu-Glu-Gly-Glu-Pro-Leu-Tyr-Arg-Arg-Ala-Leu-Arg-Cys-Val-Asp-Met-Leu (residues 20–37 SEQ ID NO:1).

Tryptic digestion of the purified ovine CRF-BP proteins is carried out, followed by purification of the tryptic fragments. The tryptic fragments from the 33 kD fraction all have counterparts in the tryptic digest pattern of the 35 kD protein. Sequence analysis of five separate tryptic fragments, following N-terminal sequencing of those fragments, produced the following AA sequences:

Phe-Pro-Ser-Ser-Gln-Asp-His-Pro-Leu-Pro-Thr (residues 96–106 SEQ ID NO:1;

Tyr-Val-Asp-Phe-Cys-Asp-Ser-Gly-Leu-Ser-Arg (residues 110–120 SEQ ID NO:1);

Ser-Ser-Ala-Gly-Cys-Gly-Gly-Ile-Gly-Asp-Phe-Val-Glu-Leu-Leu-Gly-Gly (residues 206–222 SEQ ID NO:1);

Val-Gly-Cys-Asp-His-Thr-Val-Leu-Arg (residues 248–256 SEQ ID NO:1); and

Val-Thr-Phe-Glu-Tyr-Arg (residues 267–272 SEQ ID NO:1.

The Cys residues were deduced from overall experimental data.

Following obtaining the N-terminal sequence data from the purified 33 and 35 kD brain-derived ovine CRF-BPs and these tryptic fragment sequence analyses, synthetic 5' sense and 3' antisense oligonucleotides of 21 bases each with about 55% G,C content were obtained which were directed to coding regions that were felt to be highly conserved between different mammalian species. These oligonucleotides were used to clone ovine CRF-BP gene fragments by means of Polymerase Chain Reaction (PCR) from ovine cDNA (derived from brain mRNA). Using standard PCR conditions and 35 cycles of 94° C. denaturation, 45° C. annealing, 72° C. extension, with one final extension for 10 min. at 72° C., DNA fragments of 552 and 441 base pairs (bp) were produced. These ovine CRF-BP cDNA partial clones are set forth herein as SEQ ID NO:3 and SEQ ID NO:4, respectively.

A 621 base pair pst1 fragment from the 5' end of the human serum CRF-BP cDNA coding region was labeled and used as a molecular hybridization probe to screen the lambda Zap™ sheep brain cDNA library described supra. A 678 bp ovine CRF-BP partial clone (SEQ ID NO:5) was identified.

Subsequent comparison of the corresponding amino acid sequences from the Edman degradation sequence analyses, the PCR cloned cDNA fragments, and the cDNA partial clone yields the composite amino acid sequence of the 35 kD ovine CRF-BP (SEQ ID NO:1; of the 33 kD ovine CRF-BP (residues 20–295 of SEQ ID NO:1); and of these two proteins with the 37 amino acid deletion (SEQ ID NO:2 and residues 20–258 of SEQ ID NO:2). The biologically active N-terminus which is proteolytically cleaved from the 35 kD ovine CRF-BP is also identified as residues 1–18 or 1–19 of SEQ ID NO:1.

EXAMPLE III

Ovine brain-derived membrane-associated CRF-BP Binding and Dissociation Analyses:

Antibodies directed to the peptide comprising N-terminal residues 1–25 of SEQ ID NO:6 (human CRF-BP) are able to immunoprecipitate the CRF/human CRF-BP complex. The same antibodies do not have immunoaffinity to the full length ovine 33 or 35 kD ovine brain-derived membrane-associated CRF-BPs. These antibodies with affinity toward the human CRF-BP N-terminus are not able to bind the full length human CRF-BP of SEQ ID NO:6 when 33 kD ovine brain-derived CRF-BP is added to the solution. It is thus concluded that the N-terminal epitope region of the human CRF-BP is masked from the antibody in the human CRF-BP/33 kD ovine brain-derived CRF-BP complex. It is furthermore shown that a synthetic peptide consisting of human residues 1–21 of SEQ ID NO:6 inhibits the ability of ovine CRF-BP to bind CRF, but it does not inhibit the ability of full length human serum CRF-BP to bind CRF. This is due to 70% of the brain-derived ovine CRF-BP being composed of the N-terminal truncated version (33 kD) of the 35 kD ovine CRF-BP. Therefore it is most probable that residues 1–21 of SEQ ID NO:6 (human CRF-BP) complex with the 33 kD brain-derived ovine CRF-BP but not with the full length 35 kD ovine protein. The ovine 35 kD brain-derived CRF-BP is therefore analogous to the human serum-derived CRF-BP; whereas the 33 kD truncated version and the N-terminal proteolytic cleavage product are brain-derived mammalian entities with different functions.

The synthetic 21 amino acid N-terminal human serum CRF-BP peptide does not, in itself, have affinity for CRF. The N-terminal ovine CRF-BP peptides, i.e. residues 1–18 and 1–19 of SEQ ID NO:1, likewise do not complex with CRF. The 33 kD ovine protein, however, binds CRF with high affinity ($K_D$ of 0.25). Moreover, the 21-residue synthetic N-terminal human serum CRF-BP inhibits formation of the CRF/33 kD ovine CRF-BP complex.

The 35 kD ovine CRF-BP serves partially as a precursor from which the 33 kD protein and 18 and 19 residue N-terminal proteolytic fragments are derived. The proteolytic cleavage may occur between residues 19–20 of SEQ ID NO:1 or between residues 18 and 19, with the Arg residue subsequently being trimmed. In any event, it results in a conformational change in the ovine brain-derived CRF-BP that decreases its $K_D$ for CRF from 7.5 to 0.25 nanomolar. The resulting 33 kD CRF-BP also has a tendency to complex with the 35 kD ovine CRF-BP, which complex occurs through the N-terminus of the 35 kD protein to create 35 kD/33kD ovine CRF-BP complex. Thus, the 35 kD ovine CRF-BP with its intact and exposed N-terminal 19 residue region is reactive to complex with the 33 kD version; however, the N-terminal cleaved 18 and 19 AA peptides are able to compete with the 35 kD protein and cause dissociation of the complex of the 35 kD ovine CRF-BP and the 33 kD ovine CRF-BP. It is expected that this N-terminal proteolytic product and its human brain homolog will hence be able to liberate CRF-BP CRF binding sites and thereby increase binding site density for CRF in biological tissues. This will effectively reduce the concentration of CRF in biological tissues and is therefore reasonably expected to be useful for the treatment of high level CRF related physiological disorders.

The proteolytic event which produces the 33 kD version of the brain-derived CRF-BP is important in governing the brain ratio of the 33 kD CRF-BP to the 35 kD CRF-BP. This proteolytic event therefore is critical in determining the equilibrium level of unbound CRF in the brain. The natural control mechanism in which such a brain protease partakes is a fine tuning device to control the 33/35 kD CRF-BP molecular population in the brain and thus the amount of available synaptic CRF binding sites. Therefore, therapeutically valuable peptide and analog antagonists of this protease can be provided in the form of CRF-BP fragments and synthetic chemical derivatives or analogs of sufficient length to be recognized by the native proteolytic enzyme and which also span the native cleavage site (i.e. residues 18–19 of SEQ ID NO:1 and residues 21–22 of SEQ ID NO:6). Such peptides are at least about 5 residues in length, are preferably greater than about 10 AA residues in length, and more preferably are about 15 residues or more.

EXAMPLE IV

The construction of functional genes which encode the ovine CRF-BPs is set forth hereinafter as well as methods for recombinant expression of these proteins. DNA coding regions for the mature 35 kD ovine brain-derived membrane-associated CRF-BP are constructed by fusion, in 5'–3' order of: (1) a synthetic DNA sequence which encodes residues 1–7 (using the statistically conserved human codons of the genetic code for these particular residues well known to those skilled in the art) of SEQ ID NO:1, (2) the 1–189 bp DNA sequence of SEQ ID NO:3, and (3) the DNA sequence of SEQ ID NO:5. Heterologous gene expression of this composite DNA segment contains the complete coding region for the mature 35 kD protein (SEQ ID NO:1) and is effectively carried out in Chinese hamster ovary (CHO) cells, CV-1 cells, HeLa S3, NIH-3T3 cells or COS7 cells using either commercially available expression vectors such as pMSG, pSVT7 and pMT2 from Pharmacia, Piscathaway, N.J., or the widely used Okayama-Berg vectors. Use of standard techniques produces the 295residue active mature glycosylated protein (see also, E. Potter, et al., *Nature*, 349, 423–426 (1/31/91); *Molecular Cloning, A Laboratory Manual* 2Ed, Chapter 16, Expression of Cloned Genes in Cultured Mammalian Cells, J. Sambrook et al. (1989)). Baculovirus vectors may also be used for heterologous expression of these genes in cultured insect cells as described by Summers, M. D. et al., *Tex. Agric. Exp. Stn. Bull.* No. 1555 (1987). This composite DNA segment gene can alternatively be fused to native bacterial genes to create stable chimeric procaryotic biosynthetic proteins. The chimeric proteins are easily isolated by affinity chromatography, and the active protein is then released by subsequent site-specific proteolytic cleavage. Well developed commercial bacterial expression vectors and host cells are readily available, as well as isolation/purification materials and protocols for production of these biosynthetic polypeptides (i.e. Protein Fusion and Purification System (PFP), New England Biolabs).

The evidentiary lack of digression in evolution in regard to the molecular structure of the 41 AA CRF biological messenger between rats and humans is fairly indicative of probable conserved regions in the corresponding amino acid sequences of analogous receptors and CRF brain-derived binding proteins in such diverse mammalian species. The corollary is that, once one has a significant portion of a brain-derived membrane-associated CRF-BP nucleic acid sequence of one mammalian species, i.e. the ovine sequence as disclosed herein, it is a straightforward exercise to obtain naturally occurring variant homolog sequences of other animal species which encode homolog binding proteins (see e.g., Potter et al., *Nature*, 349, 423–426 (1991), where it was shown that the cDNA coding region for human serum-derived CRF-BP was of sufficient homology to permit identification of an analogous serum-derived rat cDNA coding region). For example, using established methods well known to those skilled in the art (see e.g., *Molecular Cloning, A Laboratory Manual* 2Ed, Chapter 8, Construction and Analysis of cDNA Libraries, J. Sambrook et al. (1989)), SEQ ID NOs:3–5 or portions thereof may be used to screen mammalian cDNA libraries made from human brain mRNA to identify and isolate human brain-derived membrane-associated CRF-BP DNA homolog coding regions and/or those of other mammalian species.

Unless otherwise stated hereinbefore, all percentages are volume percents.

Although the invention has been described with regard to its preferred embodiments, which constitute the best mode permanently known to the inventors, it should be understood that various changes and modifications as would be obvious to one having the ordinary skill in this art may be made without departing from the scope of the invention which is set forth in the claims appended hereto. For example, biologically active fragments of such proteins, shortened at the C-terminus or at the N-terminus or at both termini, can be employed instead of the entire protein to have the same biological effect of modulating the bioactivity CRF.

Particular features of the invention are emphasized in the claims which follow.

What is claimed is:

1. An is isolated mammalian brain-derived membrane-associated CRF-binding protein having a molecular weight of about 35 kD as determined under reducing conditions by SDS page and an N-terminus of residues 1–16 of SEQ ID NO: 1.

2. A CRF-binding protein according to claim 1 comprising residues 1–295 of SEQ ID NO:1.

3. An isolated mammalian brain-derived membrane-associated CRF-binding protein having a molecular weight of about 33 kD as determined under reducing conditons by SDS page and an N-terminus of residues 20–37 of SEQ ID NO: 1.

4. A CRF-binding protein according to claim 3 comprising residues 20–295 of SEQ ID NO:1.

5. An isolated, substantially pure CRF-binding protein which exhibits affinity to CRF and which has a molecular weight of at least about 33 kD as determined under reducing conditions by SDS page and has the amino acid sequence of a native mammalian protein that includes at least one sequence selected from the group consisting of the following sequences of SEQ NO: 1: residues 1–16, residues 20–37, residues 110–120, residues 206–222 and residues 248–256.

6. A CRF-binding protein according to claim 5 which binds to CRF such that its dissociation constant ($K_D$) is 10 nanomolar or less.

7. A CRF-binding protein according to claim 5 comprising the amino acid residues encoded by SEQ ID NO:3.

8. A CRF-binding protein according to claim 5 comprising the amino acid residues encoded by SEQ ID NO:5.

9. A CRF-binding protein according to claim 5 comprising the amino acid sequence of SEQ ID NO:2 which binds to CRF such that its dissociation constant ($K_D$) is 10 nanomolar or less.

10. A CRF-binding protein according to claim 5 comprising residues 20–258 of SEQ ID NO: 2.

11. A CRF-binding protein according to claim 5 comprising the amino acid residues encoded by SEQ ID NO:4.

* * * * *

UNITED STATES PATENT AND TRADEMARK OFFICE
CERTIFICATE OF CORRECTION

PATENT : 5,587,462
DATED : December 24, 1996
INVENTOR(S) : Behan, et al.

It is certified that error appears in the above-identified patent and that said Letters Patent is hereby corrected as shown below:

On the title page, item [73] Assignee: should include --and the University of Reading, Reading, England--.

Column 27, line 28, Claim 1, after "an" delete "is".
Column 27, line 37, Claim 3, change "condition" to --conditions--.

Signed and Sealed this

Fourteenth Day of April, 1998

Attest:

BRUCE LEHMAN

Attesting Officer

Commissioner of Patents and Trademarks